US012742784B2

(12) United States Patent
Singh et al.

(10) Patent No.: US 12,742,784 B2
(45) Date of Patent: Sep. 22, 2026

(54) **METHOD FOR THE DETECTION OF *CLOSTRIDIUM NEUROTOXINS* USING A CHIMERIC SUBSTRATE FUSION PROTEIN**

(71) Applicant: Prime Bio, Inc., North Dartmouth, MA (US)

(72) Inventors: Bal Ram Singh, Dartmouth, MA (US); Raj Kumar, Dartmouth, MA (US)

(73) Assignee: Prime Bio, Inc., North Dartmouth, MA (US)

( * ) Notice: Subject to any disclaimer, the term of this patent is extended or adjusted under 35 U.S.C. 154(b) by 1479 days.

(21) Appl. No.: 17/339,263

(22) Filed: Jun. 4, 2021

(65) Prior Publication Data

US 2022/0390461 A1 Dec. 8, 2022

(51) Int. Cl.

| | |
|---|---|
| ***G01N 33/68*** | (2006.01) |
| ***C07K 14/245*** | (2006.01) |
| ***G01N 21/64*** | (2006.01) |
| ***G01N 27/447*** | (2006.01) |
| ***G01N 33/02*** | (2006.01) |
| ***G01N 33/487*** | (2006.01) |
| *G06N 3/02* | (2006.01) |

(52) U.S. Cl.

CPC ....... *G01N 33/6839* (2013.01); *C07K 14/245* (2013.01); *G01N 21/643* (2013.01); *G01N 27/447* (2013.01); *G01N 33/02* (2013.01); *G01N 33/48714* (2013.01); *G01N 2021/6441* (2013.01); *G01N 2333/33* (2013.01); *G01N 2333/952* (2013.01); *G06N 3/02* (2013.01)

(58) Field of Classification Search

CPC ............. G01N 33/6839; G01N 21/643; G01N 27/447; G01N 33/02; G01N 33/48714; G01N 2021/6441; G01N 2333/33; G01N 2333/952; G01N 33/542; G01N 33/56911; G01N 2333/96419; C07K 14/245; C07K 14/705; C07K 2319/50; C07K 2319/60; G06N 3/02; C12R 2001/145

USPC ........................................................... 435/24

See application file for complete search history.

(56) References Cited

U.S. PATENT DOCUMENTS

2014/0235490 A1 8/2014 Kalkum et al.

OTHER PUBLICATIONS

Marx, V. Probes: FRET sensor design and optimization. Nat Methods 14, 949-953 (2017). https://doi.org/10.1038/nmeth.4434 (Year: 2017).*

Ruge, D. R., Dunning, F. M., Piazza, T. M., Molles, B. E., Adler, M., Zeytin, F. N., & Tucker, W. C. (2011). Detection of six serotypes of botulinum neurotoxin using fluorogenic reporters. Analytical Biochemistry, 411(2), 200-209. https://doi.org/10.1016/j.ab.2011.01.002 (Year: 2011).*

Plociennik. , M. (Dec. 15, 2020). synaptosomal-associated protein 25 isoform SNAP25B. https://www.ncbi.nlm.nih.gov/protein/1018443211?sat=49&satkey=11016 (Year: 2020).*

Haenig, C. (Dec. 12, 2020). vesicle-associated membrane protein 2 isoform 1 [*Homo sapiens*]. https://www.ncbi.nlm.nih.gov/protein/172072620?sat=49&satkey=13472519 (Year: 2020).*

Bompiani, K., & Dickerson, T. (2014). High-Throughput Screening Technologies for Botulinum Neurotoxins. Current Topics in Medicinal Chemistry, 14. (Year: 2014).*

Arnon, S.S., Schechter R., Inglesby T.V., et al. (2001). Botulinum toxin as a biological weapon: medical and public health management. JAMA, 285 (20), 1059-70.

Hobbs, R. J., Thomas, C. A., Halliwell, G., et al. (2019). Rapid Detection of Botulinum Neurotoxins—A Review. Toxins, 11 (7), 418-430.

Schantz, E. J., & Johnson, E. A. (1992). Properties and use of botulinum toxin and other microbial neurotoxins in medicine. Microbiological reviews, 56(1), 80-99.

Whitemarsh, R.C., Strathman, M.J., Chase, L.G. , et al., (2012) Novel Application of Human Neurons Derived from Induced Pluripotent Stem Cells for Highly Sensitive Botulinum Neurotoxin Detection, Toxicological Sciences, 126 (2), 426-435.

Whitemarsh, R. C., Tepp, W. H., Bradshaw, M., et al. (2013). Characterization of botulinum neurotoxin A subtypes 1 through 5 by investigation of activities in mice, in neuronal cell cultures, and in vitro. Infection and immunity, 81(10), 3894-3902.

Li, L., and Singh, B. R. (1999). In vitro translation of type A *Clostridium botulinum* neurotoxin heavy chain and analysis of its binding to rat synaptosomes. Journal of Protein Chemistry, 18, 89-95.

(Continued)

*Primary Examiner* — Robert B Mondesi

(57) ABSTRACT

The present invention provides a method for detecting and assaying *Clostridium* neurotoxins and identification of serotypes of botulinum neurotoxins in various food matrices and clinical samples. This method is also used for detection of BoNT inside the neuronal and epithelial cells. The method comprises detecting and assaying the presence of a *Clostridium* neurotoxin in a sample by: exposing the sample containing a *Clostridium* neurotoxin to a sample comprising a novel SNAMPAXIN/SNAMP universal recombinant substrate fusion protein capable of producing a detectable FRET, following cleavage; detecting and assaying the presence of the *clostridium* neurotoxin by measuring a change in the energy transfer or the luminescence signal; and detecting and assaying an electrophoretic mobility pattern of one or more cleaved protein bands or a degraded protein, using a high throughput automated system to identify the different serotypes of the *Clostridium* neurotoxin. SNAMPAXIN/SNAMP is formed from parts of BoNT substrates SNAP-25 and VAMP.

19 Claims, 4 Drawing Sheets

Specification includes a Sequence Listing.

(56) References Cited

OTHER PUBLICATIONS

Froger, A., and Hall, J. E. (2007). Transformation of plasmid DNA into *E. coli* using the heat shock method. Journal of visualized experiments : JoVE, (6), 253.

Pellett S. (2013). Progress in cell-based assays for botulinum neurotoxin detection. Current topics in microbiology and immunology, 364, 257-285.

Basavanna, U., Muruvanda, T., Brown, E. W., and Sharma, S. K. (2013). Development of a Cell-Based Functional Assay for the Detection of *Clostridium botulinum* Neurotoxin Types A and E. International Journal of Microbiology, Article ID 593219, 1-7.

Bitz S (2010) The botulinum neurotoxin LD50 test—problems and solutions. ALTEX 27: 114-116.

Straughan D (2006) Progress in applying the Three Rs to the potency testing of Botulinum toxin type A. Altern Lab Anim 34: 305-313.

Taylor K, Gericke C, Alvarez LR (2019) Botulinum toxin testing on animals is still a Europe-wide issue. ALTEX 36: 81-90.

* cited by examiner

Lane 1 MW
Lane 2 Cell Lysate
Lane 3 Flow Through
Lane 4 Wash
Lane 5-10 Different Fractions

METHOD FOR THE DETECTION OF *CLOSTRIDIUM NEUROTOXINS* USING A CHIMERIC SUBSTRATE FUSION PROTEIN

FIELD OF INVENTION

The present invention relates to a new recombinant substrate that will detect *Clostridium* neurotoxin, especially all the serotypes of botulinum neurotoxin in their enzymatically active state. The new recombinant substrate is called SNAMPAXIN, and it is based on a known sequence of botulinum neurotoxin (BoNT) substrates SNAP-25 and VAMP, which are flanked by red fluorescent protein (RFP) and green fluorescent protein (GFP). The cleavage of the substrate by biologically active *Clostridium* neurotoxin will result in the Förster resonance energy transfer (FRET) signal change for the detection. Detection and identification serotype of the *Clostridium* toxin is based on the electrophoretic mobility pattern of cleaved protein bands using a high throughput automated system. Identification of BoNT A or BoNT C in the sample can be achieved by treating with SNAMPAXIN, which will show two extra bands at 31 kDa and 12 kDa, in case of serotype BoNT C. The method can be used to assay the functional state of botulinum neurotoxins in cultures and formulations of therapeutic products of different types of botulinum neurotoxins.

SEQUENCE LISTING TEXT FILE

A text file entitled "Sequencelisting 5ID_ST25" is submitted with this application. The date created is Apr. 6, 2021 and the file size is 20 KB; and corrected with "Sequence listing 3ID_ST25" created on Jul. 28, 2021, wherein the file size is also 20 KB.

BACKGROUND OF THE INVENTION

*Clostridium* neurotoxins, especially botulinum neurotoxins (BoNTs), are the most lethal and potent molecules known. Botulinum neurotoxin is the causative agent for infant, wound, foodborne and iatrogenic botulism. The lethality and potency of the molecule results from proteolysis of SNARE proteins, which are involved in neurotransmitter release. In addition, *Clostridium* neurotoxins, especially BoNT, pose several threats to the public health. First, it poses a concern for the food industry and military personnel due to the potential threat of contamination. Second, wound and infant botulism cases are increasing in the United States. The most common form of botulism in the U.S. is infant botulism with approximately 80-100 US infants annually. Of the seven serotypes of BoNT (A-G), serotypes A, B, E, and F are known to cause human botulism. BoNTs are large proteins with a molecular weight of 150 kDa, which are produced in the form of a complex of 150 kDa neurotoxin and 4-5 neurotoxin associated proteins (NAPs). Each of the seven toxins is composed of a heavy chain (100 kDa), which mediates the entry of toxin into neurons, and a light chain (50 kDa), which functions as a zinc-dependent endopeptidase inside cells.

Terrorists have already attempted to use botulinum toxin as a bioweapon. Aerosols were dispersed at multiple sites in downtown Tokyo, Japan, and at U.S. military installations in Japan on at least 3 occasions between 1990 and 1995 by the Japanese cult Aum 2wShinrikyo, though these attempts failed due to the faulty microbiological technique, deficient aerosol-generating equipment, and/or internal sabotage. BoNTs are also weaponized by rogue countries as a weapon of mass destruction.

Currently, rapid diagnostic methods are not available for the rapid detection of *Clostridium* neurotoxin and no antidotes are known that can reverse the paralysis caused by BoNT. Therefore, patients with botulism have to be put under respiratory intensive care. Further, the paralysis caused by BoNT can last for months. The estimated cost for each botulism patient under respiratory supportive care could be as high as $350,000. This puts a large burden on hospitals, both financially and resource-wise. Due to these reasons, *Clostridium* neurotoxins such as tetanus toxins and BoNTs create a maximum fear among populations concerned with bioterror agents and pose a significant threat to homeland security.

Biological threat agents and toxins with high lethality are of great concern as they are relatively easy to acquire, cultivate and can potentially be used for terrorist activities. In most cases, because of the extreme lethality of the toxins, rapid diagnosis of intoxicated individuals soon after exposure is critical to categorically determine the type and extent of the intoxication. This is also vital to devise suitable treatment and remedial measures. This necessitates the development of assays that are highly sensitive to the presence of the toxins from diverse clinical samples.

Detection of low levels of BoNT in a sample using prior art methods is difficult. However, due to the enormous potency of the toxin, which can be lethal for humans in systemic doses of 1 to 2 ng/Kg body weight (Arnon 2001), these low levels can be extremely dangerous. For example, in infant botulism (IB), a condition in which a baby's intestines have become colonized by toxin-secreting *Clostridium botulinum* bacteria, it is possible to detect BoNT in stool samples (Hobbs et al., 2019). However, attempts to diagnose IB serologically via detection of BoNT in the blood have been deemed unreliable (Schantz 1992).

Botulinum poisoning is a serious and well-recognized biothreat. Botulinum neurotoxins (BoNT) are extremely potent, relatively simple to prepare and disburse and have already been used as an agent of bioterror. It is in the category A agent list (the only toxin on this list) of the National Institute of Allergy and Infectious Diseases (NIAID) biodefense agents and the Centers for Disease Control and Prevention (CDC) select agents. Due to its potential as a bioterror agent, strong efforts are being made for detection, prevention and treatment of botulism. Several assay methods have been developed over the years; however, most of the assay formats detect highly purified BoNT samples and not the samples in complex matrices with similar sensitivity. There are two aspects of botulinum neurotoxin detection in different samples: a) a Structural aspect, which is relatively easy to detect and quantify with techniques like enzyme linked immunosorbent assay (ELISA); and b) a Functional aspect, which is relatively difficult, used for both qualitative and quantitative detection, with methods like a mouse bioassay, which is extremely expensive.

Another level of challenge in the functional assay is multiplexing. Although several platforms based on ELISA (Enzyme Linked Immuno Sorbent Assay) format are available to perform multiplex assays, these can detect both active and inactive toxin without differentiating them. Fast and sensitive detection of active toxin is very important to reduce the time of diagnosis and for the food industry. Mouse bio-assay (MBA) is a very sensitive method, however, it requires at least 48 hours and is inconvenient for field conditions. Furthermore, it is very expensive in addition to ethical issues. This assay monitors the presence of specific botulism symptoms after intraperitoneal injection of the suspect material into mice. The samples can be pre-incubated and injected with specific antisera to any of BoNTs, hence the serotype of BoNT present in the sample can be determined. The mouse bioassay method consists of a three-part protocol: in a screening assay, a limited number of sample dilutions are made and injected into mice and the animals are observed for 48 hours; if the mice die of a botulism symptom, the sample is diluted further and injected until a dilution that does not kill mice is found; after the end point is reached the toxin type is determined by a toxin neutralization assay. At each stage of analysis, the mice are observed for 48 hours. The sensitivity of the mouse bioassay is measured as MLD (minimum lethal dose), which is contained in the highest dilution killing both (or all) mice inoculated. The sensitivity of the mouse bioassay is 2 MLD/ml (injection volume is 0.5 ml) or about 20 μg/ml toxin for type A.

While the mouse bioassay (MBA) has been considered as the "gold standard" against which the any proposed new methods are compared, there are several shortcomings associated with it:

i. mice can die non-specifically during the process;
ii. the test takes about four days to complete and it is labor intensive;
iii. it requires a special animal facility and highly trained and immunized personnel to carry out the test; and
iv. the mouse bioassay is not suitable for routine quantification of samples and cannot meet the testing capacity in the event of a real biodefense deployment due to the large number of animals needed to obtain statistically significant results.

In addition, there are ethical issues of using animals for such testing. There are several expensive peptide-based substrates available in the market; however, none of them are suitable for multiplexing.

Therefore, there is a need for developing a readily available rapid diagnostic test to detect the *Clostridium* neurotoxins. Also, a high-throughput assay would be beneficial to the food industry. On the other hand, the potential severity and lethality warrants a sensitive and serotype specific detection. Faster methods include various ELISA (Enzyme Linked Immuno Sorbant Assay), FRET (Fluorescence Resonance Energy Transfer), mass spectrometry, and PCR (Polymerase Chain Reaction) based assays. They are either expensive or have difficulty in multiplexing to detect all serotypes using a single protocol.

The assays developed so far to replace or supplement MBA, can be divided into two categories: a) toxin detection assays that detect active as well as inactive toxin; and b) endopeptidase assays that detect the catalytic activity of the BoNT light chain. The active BoNT has a few important aspects of intoxication: binding to the cell surface receptor; endocytosis and channel formation; translocation of light chain; disulfide bond cleavage and proteolytic cleavage of target proteins. The endopeptidase or proteolytic activity is the endpoint of intoxication, but other steps are equally important in the actual environment. In order to reliably measure BoNT activity, an assay should involve all aspects of the intoxication. In vitro detection assays were not able to address this concern. The only assay, other than MBA, which involves all of these steps of intoxication is a cell-based assay.

While developing new reagents or techniques to replace the MBA method, the new method should ideally recognize all the known *Clostridium* neurotoxins. A unique feature of the catalytic domain of tetanus neurotoxin and BoNT is that they all contain identical $Zn^{2+}$-binding motif in the active site. The substrates are either different SNARE (Soluble N-ethylamide Attachment Receptor) proteins or have different cleavage sites within the same protein. Specificity of the cleavage site comes from the fact that the enzyme recognizes the tertiary structure of its substrate. Each of the BoNT serotypes and tetanus neurotoxin are extremely substrate selective (except for BoNT/C) with specific cleavage sites, which is shown in the prior art Table 1. Also, due to the requirement of the tertiary structure for substrate recognition, use of short peptides with a cleavage site does not provide the specificity and recognition required for the detection of the active enzyme. For simultaneous detection of tetanus and all serotypes of BoNT neurotoxins, a substrate is needed which has cleavage sites for each of the BoNTs available with appropriate length of the substrate required for proper recognition.

US patent application 20140235490 A1, which published on Aug. 21, 2014, discloses a method of detection of BoNT in an enriched sample using luminogenic substrate capable of producing luminogenic signal following modification of substrate by BoNT. However, each serotype of BoNT requires a different substrate for detection. The detection of serotype of toxin is by exposing the BoNT modified substrate fusion protein to a detection fusion protein, thereby permitting the binding of the modified substrate fusion protein to detection protein and thereby detecting and assaying the BoNT by measuring change in light emission.

Another aspect of BoNT is its therapeutic use to treat various diseases. During the process of the therapeutic batch release many animals are sacrificed. There is a severe need of the BoNT potency detection assays corroborating to three Rs: reduced, refine and replace the use of animals in pharmaceutical industry (Straughan, 2006). Even though many cell based assays have been developed and validated to replace the animal assays, as per recently reported numbers at various places pharmaceutical industries exceeds the use of 600,000 animals worldwide (Bitz, 2010), and the animal used in Europe have estimated to be 400,000 animals per year in 2018 (Taylor et al., 2019).

Hence, there is a need in the infectious diseases-diagnostic industry for a reliable method of detection, and assay of BoNT-based therapeutic products for all the serotypes of BoNT using a universal substrate (SNAMP).

SUMMARY OF THE INVENTION

The present invention comprises a novel substrate that can detect the *Clostridium* neurotoxin with serotype specificity. Further, the present invention provides a universal substrate for all the known serotypes of botulinum neurotoxin. A further advantage of this universal substrate is that the developed method is based on the pattern recognition of cleavage of substrate for each *Clostridium* neurotoxin. Also, this method will detect and assay the active toxin in a given sample while identifying the serotype of the BoNT at the same time. The present invention will be useful for detecting and assaying the *Clostridium* neurotoxin in a sample using Förster resonance energy transfer, or a luminescence signal change, following cleavage of the recombinant substrate fusion protein by *Clostridium* neurotoxin. It will also identify the different serotypes of *Clostridium* neurotoxin using a high throughput automated system.

In the present invention, an innovative FRET sensor is created, based on a universal substrate (SNAMP), which is expressed inside a mammalian neuronal cell as fusions of green/cyan florescent protein (GFP/CFP) and red/yellow fluorescent protein (DsRED/YFP) containing the protein sequence of human SNAP25 (amino acid 141-206 of SEQ ID NO: 1) and human VAMP (amino acid 27-94 of SEQ ID NO: 4). Cleavage of this reporter by neurotoxin is used as a tool for detection of the *Clostridium* neurotoxin. Currently, no such system exists, and it is not only highly innovative, but also highly practical and useful. For detection, either a loss of FRET signal or an increase in donor signal is used. Furthermore, confirmation and validation are performed by analyzing the Western blot to compare and validate the findings of fluorescence analysis. Compared to the mouse bioassay/lethality assay, the assay of the present invention has the following advantages: (1) no need for a large number of animals (sacrificing one animal can generate enough cells for several assays); (2) higher specificity due to the use of BoNT substrate cleavage as an endpoint; (3) statistically reproducible results; (4) safer protocols for laboratory workers as the toxin injection is not needed; and (5) stable and sensitive primary cells. Initial developmental cost of this assay may be high, but once the laboratory has a facility of producing its own primary neurons, cost will be reduced significantly.

While FRET assays for a single serotype of BoNT are conducted either under in vitro conditions or as a cell bioassay, the present approach of using a universal substrate for a cell bioassay addresses the need of public health safety.

A main object of present invention is to provide a method for detecting and assaying the presence of a *Clostridium* neurotoxin in a sample comprising:

a. exposing the sample containing a *Clostridium* neurotoxin to a sample comprising a recombinant substrate fusion protein capable of producing a detectable Förster resonance energy transfer/Luminescence signal change following cleavage of recombinant universal substrate fusion protein by the *Clostridium* neurotoxin;
b. detecting and assaying the presence of the *Clostridium* neurotoxin by measuring a change in Förster resonance energy transfer signal in the sample; and
c. further determining electrophoretic mobility pattern of cleaved substrate bands, using a high throughput automated system to identify the serotype of the *Clostridium* neurotoxin.

Another objective of the present invention is to develop a validated cell-based assay for the detection of all serotypes, which could be used as a replacement of MBA.

Another object of the present invention is to develop a method for detection of *Clostridium* neurotoxin by providing a universal substrate.

Another object of the present invention is to provide a universal substrate for detection of *Clostridium* neurotoxin.

Yet another object of the present invention is to identify each serotype of BoNT.

Yet another object of the present invention is to provide a method of preparation of the universal substrate.

In an embodiment, the *Clostridium* neurotoxin is tetanus neurotoxin or botulinum neurotoxin.

In an embodiment, the botulinum neurotoxin is botulinum neurotoxin type A, B, C, D, E, F and G.

In an embodiment, the botulinum neurotoxin is in the active form.

Another aspect of present invention is that the recombinant substrate fusion protein comprises of:

a. a fragment of human SNAP-25 sequence of SEQ ID NO: 1;
b. a fragment of human VAMP sequence of SEQ ID NO: 4;
c. optionally, a fragment of syntaxin of SEQ ID NO: 5; and
d. a Förster resonance energy transfer (FRET) or luminescence reporter;

Another aspect of present invention is that the recombinant substrate fusion protein SNAP-25 and VAMP sequence (SNAMP) is in between the FRET Reporter.

In another aspect of present invention is that the fragment of human SNAP-25 sequence is amino acid 141 to amino acid 206 of SEQ ID NO: 1.

Another aspect of present invention is that the fragment of human VAMP sequence is amino acid 27 to amino acid 94 of SEQ ID NO: 4.

Another aspect of present invention is that the FRET reporter comprises: Enhanced Green Fluorescence Protein (EGFP), red fluorescent protein (RFP), cyan fluorescent protein (CFP), yellow fluorescent protein (YFP), blue fluorescent protein (BFP) or combinations thereof.

Another aspect of present invention is that the recombinant substrate fusion protein comprises fragment of human SNAP-25 sequence of SEQ ID NO: 1 and a fragment of human VAMP of SEQ ID NO: 4 to provide a SNAMP recombinant substrate fusion protein.

Another aspect of present invention is that the recombinant substrate fusion protein comprises of a fragment of the human SNAP-25 of SEQ ID NO; 1, a fragment of human VAMP of SEQ ID NO: 4, and a FRET or luminescence reporter to provide a recombinant universal substrate fusion protein, SNAMP.

Another aspect of present invention is that the recombinant substrate fusion protein comprises fragment of human SNAP-25 of SEQ ID NO; 1, a fragment of human VAMP of SEQ ID NO; 4, and a fragment of syntaxin (a.a. 221-264) of SEQ ID NO: 5, to provide SNAMPXIN (SNAP25-VAMP-SYNTAXIN) of SEQ ID NO: 3, recombinant substrate fusion protein.

Another aspect of present invention is that the recombinant substrate fusion protein comprises fragment of human SNAP-25 sequence of SEQ ID NO: 1, a fragment of human VAMP sequence of SEQ ID NO: 4, a syntaxin and a Förster resonance energy transfer (FRET) or Luminescence reporter to provide another recombinant universal substrate fusion protein, SNAMPAXIN.

Another aspect of present invention is that the FRET reporter is EGFP and RFP.

Another aspect of present invention is that the FRET is CFP and YFP.

Another aspect of present invention is that if the botulinum neurotoxin is serotype A or C, the serotype is differentiated using SNAMPAXIN:

a. wherein exposing the sample containing a botulinum neurotoxin A or C to a SNAMPAXIN recombinant protein that is capable of producing a detectable Förster resonance energy transfer signal change following cleavage of recombinant SNAMPAXIN by the botulinum neurotoxin;
b. detecting and assaying the presence of the *clostridium* neurotoxin by measuring a change in Förster resonance energy transfer signal in the sample; and
c. further determining electrophoretic mobility pattern of cleaved protein bands or degraded protein, using a high throughput automated system to identify the serotype of *Clostridium* neurotoxin;
d. wherein serotype C of botulinum neurotoxin shows one extra band of ~31 kDa and 12 kDa.

Another aspect of present invention is that the recombinant substrate fusion protein is expressed in *E. Coli*; and using the vector of FIG. 1.

Another aspect of present invention is that the recombinant substrate fusion protein is optionally tagged by GST or Histidine.

Another aspect of present invention is that the recombinant substrate fusion protein is of SEQ ID NO: 3.

Another aspect of present invention is that the sample is food sample or blood or serum sample of human or animal.

Another aspect of present invention is that the endopeptidase cleavage site is in the recombinant full-length substrate, SNAP-25.

Another aspect of present invention is that the endopeptidase cleavage site is in the recombinant full-length substrate, VAMP.

Another aspect of present invention is that the RFP and EGFP are attached at N-terminal and C-terminal, and vice versa.

Another aspect of present invention is that the CFP and YFP are attached at N-terminal and C-terminal, and vice versa.

Another aspect of present invention is that the SNAP-25 and VAMP (either full length or truncated version of the substrate) is linked by FRET reporters (EGFP-RFP or CFP-YFP).

Another aspect of present invention is the process for the preparation of novel universal substrate comprising steps of:

a. Induction of *E. coli* culture $OD_{600}$=0.8-1.0 by adding 1 mM IPTG
b. Growing culture for 25° C. at 16-18 hr.
c. The cell paste suspends in 1×PBS.
d. Sonicate for a period of 3 minutes (3-5 sec on/off pulse) at 4° C. on cold beads.
e. Centrifuge the culture for 60 to 90 minutes at 12000 rpm at 4° C.
f. Supernatant is collected; and
g. Supernatant purified using glutathione or Ni-NTA affinity column.
h. Combine the pool after elution using 20 mM glutathione, and concentrate the pool by using Centriprep-30.

Another aspect of present invention is that the pH of buffer in the range of 7.2 to 8.0, preferably 7.5.

Another aspect of present invention is that the concentration of glutathione solution is 5 mM, 10 mM, 15 mM, 20 mM, 25 mM and 30 mM concentration of imidazole solution is 10 mM, 50 mM, 100 nM, 200 mM and 500 mM.

Another aspect of present invention provides a process for preparation of recombinant novel substrate comprising steps of:

a. pBR322 vector was used for cloning the novel universal substrate (SNAMP) in a BL21(DE3) or NEB-5α strain for expression of the plasmid;
b. FRET reporter (GFP/RFP pair) was linked to full length or truncated version of SNAP-25 and truncated version of VAMP; and
c. Purified the protein with one significant band at ~95 kDa and three less prominent band at ~62 kDa, ~56 kDa and 33 kDa protein position using Glutathione column.

Another embodiment of the present invention provides that in the process the strain used for expression of the plasmid *E. coli* BL21 (DE3).

Another embodiment of the present invention a process wherein the strain used for expression of the plasmid *E. coli* or NEB strains.

Another embodiment of the present invention a process wherein form of substrate (either full or truncated) was selected from the neuronal substrates of botulinum toxin.

Yet another embodiment of the present invention is the composition used for the detection of botulinum toxin in various foods and clinical matrices.

Yet another embodiment of the present invention is the composition used for the detection of botulinum toxin in cell-based detection methods using transfection protocols. In this embodiment the GST-tag for purification is not needed for cell-based assay, and a new reconstruct a plasmid with GFP/CFP-SNAP25-VAMP-RFP/YFP utilized. This sensor is transfected to a neuronal cell. Rapid detection of the presence of a biologically active BoNT, FRET technique will be used.

In another embodiment, the protocol for transfection is optimized for transfection of the universal substrate based FRET sensor in a mammalian neuronal cell.

In another embodiment primary neuronal cells are better alternative because, as continuous cell lines differ in their sensitivity to BoNT serotypes based on surface receptors, ganglioside profiles, and other often not well-defined characteristics.

Whereas, primary neuronal cells present a better alternative which can be used to study all BoNT serotypes, in another embodiment HiPSC (Human-induced Pluripotent Stem Cells) neurons is used as these are more sensitive than RSC (Rat Spinal Cord) for BoNT/A1. However, HiPSC do not express adequate amount of receptors, such as SV2B, SV2C, SYT2 and VAMP in comparison to RSpN (Rat Spinal Cord Neurons) (Whitemarsh et al., 2012). Spinal cord neurons is the most relevant and sensitive BoNT cell model (Whitemarsh et al., 2013).

In yet another embodiment, the universal substrate is transfected in any other neuroblastoma cells available for culturing, including but not limited to Neuro2A, SHSY5Y, PC12 or derived cells, chromaffin cells, M17 cells, human adrenergic SK-N-SH cell line and NS-26 cell line, etc.

In another embodiment the cleavage of the substrate occurs inside the cell with a change in the fluorescence signal through fluorescence microscope and/or with another fluorescence monitoring tool.

In another embodiment, the immunological technique such as Western blot is used to correlate the findings of fluorescence measurement.

In another embodiment, the universal substrate is human SNAMP consisting or comprising of SEQ ID NO: 2.

Another aspect comprises a composition, an assay, and/or a vector comprising a universal substrate fusion protein comprising the amino acid sequence of any one of SEQ ID NOS: 1-5, or any combination thereof.

DETAILED DESCRIPTION OF THE INVENTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

The present invention employs the use of a novel universal substrate of the present invention for the detection of *clostridium* neurotoxin, especially serotypes of botulinum neurotoxin (BoNT). *Clostridium botulinum* produces seven serotypes of botulinum neurotoxins (A-G). The 150 kDa BoNT consists of a 100 kDa heavy chain (HC) and a 50 kDa light chain (LC) linked through a di-sulfide bond. The HC plays an accessory role of binding to neuronal cells and the trafficking of the LC into the cytosol. The intracellular toxic action of the BoNT is caused by the endopeptidase activity of the LC, which is a zinc metalloprotease enzyme. A unique feature of the catalytic domain of BoNT is that while the seven BoNT serotypes contain identical $Zn^{2+}$ binding motif in the active site, the substrates are either different proteins, or have different cleavage sites within the same protein. Each of the BoNT serotypes is extremely substrate selective (except for BoNT/C) with specific cleavage sites as shown in prior art Table 1. Specificity of cleavage site comes from the fact that the enzyme recognizes the tertiary structure of its substrate.

TABLE 1

Prior Art
Table 1: Substrates and cleavage sites of different serotypes of botulinum and tetanus toxin

| Toxin Type | Substrate | Cleavage Site |
|---|---|---|
| BoNT/A | SNAP-25 | $Gln^{197}$-$Arg^{198}$ |
| BoNT/B | VAMP | $Gln^{76}$-$Phe^{77}$ |
| BoNT/C | SNAP-25 | $Arg^{198}$-$Ala^{199}$ |
| BoNT/D | VAMP | $Lys^{59}$-$Leu^{60}$ |
| BoNT/E | SNAP-25 | $Arg^{180}$-$Ile^{181}$ |
| BoNT/F | VAMP | $Gln^{58}$-$Lys^{59}$ |
| BoNT/G | VAMP | $Ala^{81}$-$Ala^{82}$ |
| TeNT | VAMP | $Gln^{76}$-$Phe^{77}$ |
| BoNT/C | Syntaxin | $Lys^{253}$-$Ala^{254}$ |

Due to the requirement of the tertiary structure for substrate recognition, the use of short peptides with cleavage site does not provide the specificity and recognition required for the detection of the active toxic enzyme. Therefore, a novel substrate has been developed for the detection and identification of *Clostridium* toxin, especially all BoNT serotypes causing human botulism. The substrate developed is not only capable of detecting and assaying the presence of *Clostridium* neurotoxin; but, it also helps in detecting and assaying different serotypes of BoNT and tetanus. For this the present inventors have developed novel SNAMP (SEQ ID NO: 2) and SNAMPAXIN chimeric protein (SEQ ID NO: 3).

Preparation of SNAMP

Figure 1:
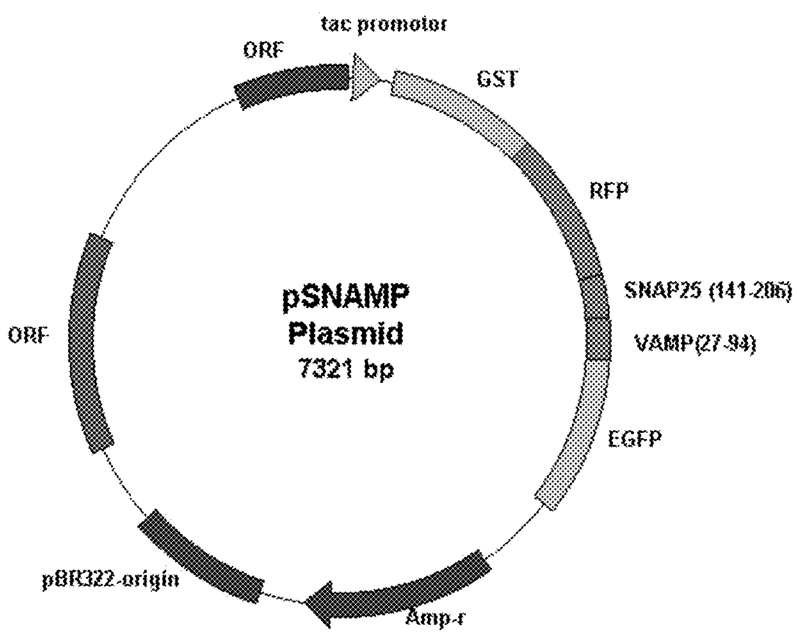
FIG. 1 shows a plasmid map of universal substrate, which is 7321 bp in length, comprising GST (Glutathione-S-transferase), RFP (Red Fluorescence Protein), SNAP-25 (Synaptosomal Associated Protein; 141-206), VAMP (Vesicle Associated Membrane Protein; 29-96), and EGFP (Enhanced Green Fluorescence Protein).

The present invention comprises a designed, cloned, expressed, and purified chimeric protein herein referred to as "SNAMP" of SEQ ID NO: 2; and comprising: SNAP25 (141-206)-VAMP (27-93)), which has cleavage sites for all the serotypes of BoNT and tetanus neurotoxin. This chimeric protein is tagged with GST for purification. Another embodiment of this invention is to clone the SNAMP gene in the His(6×) containing pBR322 vector containing tac promoter to obtain a His-tagged SNAMP, using standard cloning protocols that are readily known to those skilled in the art and widely carried out in laboratories (Li and Singh, 1999). Using a pattern recognition method of cleavage products of SNARE, chimeric protein detection of *Clostridium* toxin and serotype of BoNT was achieved. The design of this plasmid is shown in FIG. 1. The recombinant SNAMP substrate on its N-terminal is tagged with glutathione-S-transferase (GST). DNA sequences corresponding to SNAP-25 and VAMP2 fragments were inserted between RFP and EGFP sequences, all synthesized by Life Technologies (Carlsbad, CA), yielding a GST-RFP-SNAP25-VAMP-EGFP construct. The resultant recombinant plasmid was transformed in *E. coli* bacteria [strain BL21(DE3)] through heat shock method (15 seconds at 42° C.) (Froger and Hall, 2007; Li and Singh, 1999). The transformed vector was grown on an agar plate containing ampicillin (100 μg/ml), which allowed selective growth of bacterial cells containing the recombinant plasmid. Isopropyl β-D-1-thiogalactopyranoside (IPTG), 1 mM, was used to induce expression of the recombinant protein. Purification of the recombinant protein was carried out by using a general protocol of GST-affinity chromatography.

In the preferred embodiment, the cell paste (from 1 litre culture) was suspended in about 15 ml, 1×PBS pH 7.4 (called basic buffer), added with protease inhibitors. After sonication, the cell lysate was centrifuged at 12,000 rpm for about 1 hour by using Thermo Scientific Sorvall Legend RT Centrifuge and FIBERLite F15-8x50C rotor, then the supernatant is poured into a clean tube. The extract is thus obtained and is loaded to the pre-equilibrated GST or Ni-NTA column.

Figure 2:
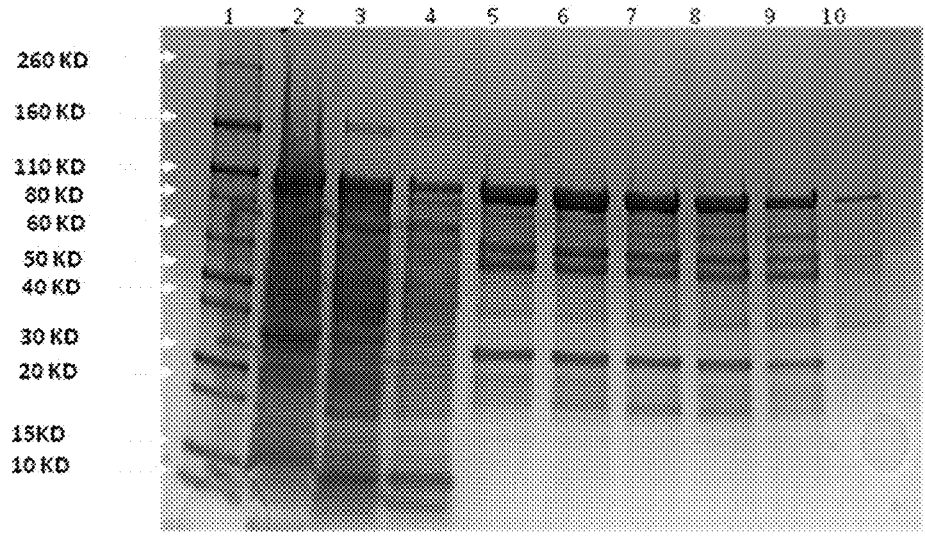
FIG. 2 shows the results of purification of the recombinant universal substrate using GSH-(Glutathione) affinity column chromatography.

After loading to the GST or Ni-NTA column, 1×PBS or 10 mM imidazole was added to the basic buffer as a washing step, respectively. Then protein binding to the column was eluted by either by 20 mM glutathione (in case of GST tag) or 200 mM imidazole (in case of His-tag). Next, the pool was combined, which had less contaminated bands; and the pool was concentrated by using Centriprep-30. After concentration, the protein concentration was measured by UV. Purification results of SNAMP obtained in this embodiment are shown in FIG. 2. The SNAMP sequence is the SEQ ID NO: 2.

Cleavage Assay

Figure 3:
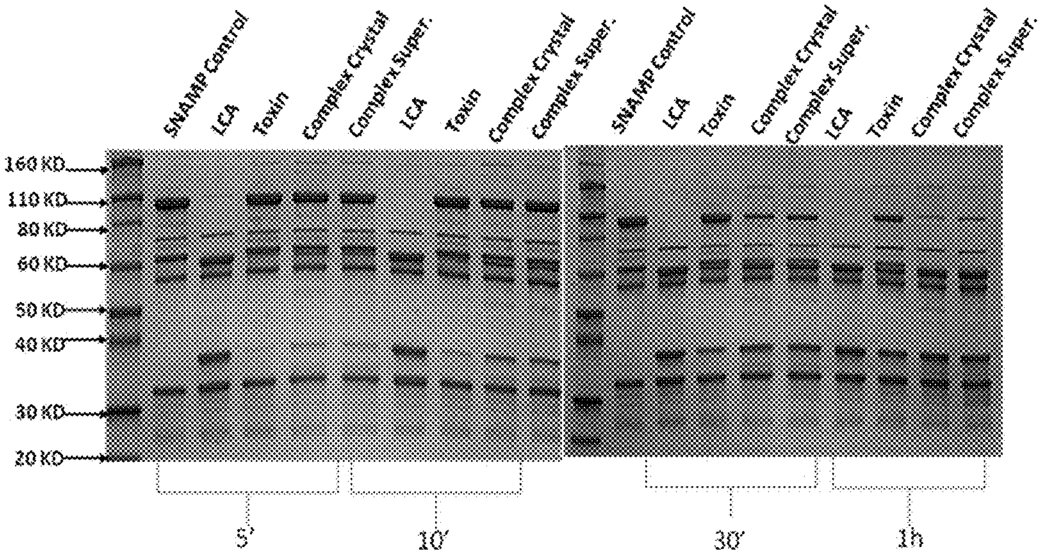
FIG. 3 shows the results of in vitro cleavage (SDS-PAGE) of recombinant universal substrate by LCA (Light chain of BoNT/A), LCB (Light chain of BoNT/B), LCE (Light chain of BoNT/E), LCT (Light chain of Tetanus Neurotoxin), BoNT/A toxin and BoNT/A Complex.
Figure 4:
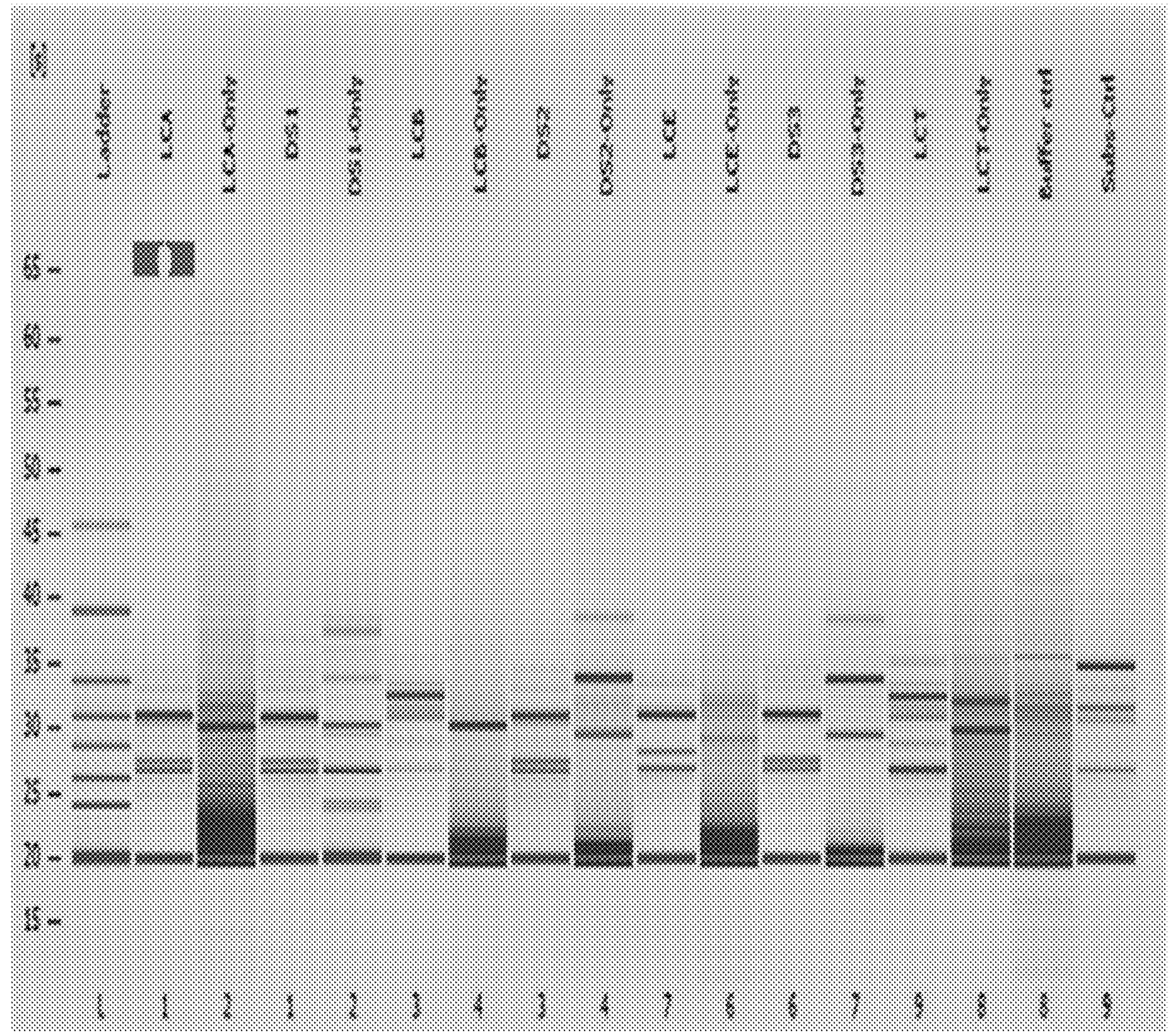
FIG. 4 shows the cleavage pattern (electropherogram) of the cleavage product after the reaction of the universal substrate with LCA, LCB, LCE, LCT, BoNT/A Toxin and BoNT/A complex using agilent bioanalyzer.

As mentioned supra, BoNT serotypes cleave their unique substrates at different sites, thus generating a different pattern of cleaved products on a monitoring platform. In a set of experiments to demonstrate endopeptidase activity of three different serotypes and forms of BoNT and TeNT, 50 nM of the enzyme was incubated with 5 μM of SNAMP substrate in a reaction buffer (1×PBS, pH 7.4) containing 2 mM DTT. The reaction was allowed for 1 hr at 37° C. and was stopped with the addition of 0.8×SDS-PAGE sample buffer. The reaction was monitored on a SDS-PAGE gel (FIG. 3). Not only the target SNAMP band at 95 kDa, but also the degraded protein bands in the preparation acted as substrates of BoNT enzymes (~62 kDa band in case of BoNT/A and BoNT/E light chains; ~34 kDa in case of BoNT/B light chains). Because of the specificity of cleavage site, each enzyme generated a unique pattern of protein bands (as shown in FIG. 3). This unique pattern is different for reach serotype of BoNT and Tetanus Toxin, which was used to differentiate the toxins. Interestingly, the BoNT/A complex, which is the likely form of toxin to be encountered as a biothreat agent cleaves the SNAMP producing exactly the same pattern as BoNT/A light chain (LCA; FIG. 3). It is also notable that BoNT/B LC (LCB) and TeNT LC (LCT) have an identical cleavage site on VAMP, but showed a slightly different pattern with SNAMP, possibly due to a difference in reaction kinetics. However, in the low throughput analysis, the cleavage product is scanned with the SDS-PAGE gel (FIG. 3) along with the BioRad™ imaging systems; and in the high throughput analysis, the cleavage product is scanned along with the electropherogram obtained using Agilent™ bioanalyzer (FIG. 4). Both SDS-PAGE and Agilent™ bioanalyzer data were similar.

Cellular Assay System

To build a universal BoNT sensor that can detect the cleavage of all the serotypes of botulinum toxin inside a sensitive neuronal cell, the plasmids with AcGFP-SNAMP-DsRed or variant constructs are transfected into primary rat spinal cord neuron cells (RSpN). Reasons for selecting the primary cell, RSpN, are as follows: a) it is a highly sensitive cell for toxin detection (BoNT/A sensitivity (EC50) is 0.3-1.0 unit (Pellett, 2013); b) it has significant expression of all the receptors required for BoNT uptake; and c) it is a perfect system to develop rapid detection of SNARE cleavage.

To culture RSpN cells, a 24 well plate is first coated with Neuron coating solution I (Cell Application Inc., CA). Thawed RSpN cells (Cell Application Inc., CA) are transferred into a 50 ml tube and Rat Neuron Plating medium (Cell Application Inc., CA) is added. After gentle mixing, the cell suspension in the 50 ml tube is pipetted and aliquoted into each well of the pre-coated 24-well plate. Cells are grown in a 37° C., 5% $CO_2$ humidified incubator. After 24 hours (h), media is changed to Rat Neuron Culture medium (Cell Application Inc., CA). Cells are maintained by changing half of the Rat Neuron Culture medium every three day. After maturation, cells are transfected with plasmids. For transfection, the NeuroPORTER (Amsbio, CA) transfection reagent is used and transfection of the construct is performed according to the manufacturer's protocol. After two hours of incubation (with the mixture of transfection reagents and plasmid), one additional volume of fresh culture medium containing a 2× concentration of B27 onto the cells is added. This assay can readily be developed by an artisan in 6-well, 12-well or 96-well formats, too, depending on the requirement.

Measurements of energy transfer are used for measuring the intracellular enzymatic activity. The FRET mechanism is by the fluorescence emission spectrum of the energy donor chromophore overlaps the absorption spectrum of the energy acceptor chromophore, and distance between donor and acceptor should be within 10-100 Å. In one of the constructs, GFP-SNAMP-RFP, GFP and RFP are the donor and acceptor, respectively, with a Förster distance of the pair as 57 Å. The GFP-RFP FRET pair is successfully used (Basavanna et al., 2013) for the full-length SNAP-25 with 206 residues, and also with the SNAMP substrate of 134 residues. The endpoint of the FRET analysis obtains significant FRET frequency ($I_{FRET}/I_D$ should be greater than $I_{FRET}/I_A$, where I, D and A is intensity, donor and acceptor, respectively) or fluorescence emission ratio from both reporters after incubation with different concentrations of BoNT toxins for 24 and 48 h. This helps in reducing the time by 50-75% compared to MBA.

For faster detection of the toxins, the cultures are incubated with stimulation buffer; 10 mM HEPES (pH 7.4) containing 56 mM KCl, 82 mM NaCl, 2 mM $CaCl_2$, and 1 mM $MgCl_2$ is adjusted to 325 mOsm with sucrose for 4 min at 37° C., along with BoNT. BoNT-containing buffer is then removed by aspiration and cells rinsed with toxin free minimal essential medium (MEM). The culture is incubated at 37° C. in MEM for an additional few hours (6-12 h, depending on the optimized toxin concentration) and used for further experimentation.

The GFP/RFP construct design is based on the following two considerations:

a) long excitation wavelength of GFP (484 nm), which aid in preventing phototoxicity; and b) brightness of GFP/RFP signal, which provides higher signal to noise ratio. The RFP photo may get bleached easily, which can reduce sensitivity or give a false reading. This is avoided by either having a shorter exposure time at a higher intensity of excitation light, or having a less intense excitation light with a longer exposure.

SNAMPAXIN is purified using similar a protocol as SNAMP. The protein sequence of SNAMPAXIN is listed in SEQ ID NO: 3.

SNAP25 is the substrate for BoNT/A and BoNT/C toxin. But the cleavage site is just one amino acid apart. So, by using SNAMPAXIN, the artisan can distinguish between these two toxins in the sample. Whereas SYMPAXIN has both SNAP25 and Syntaxin. In SDS-PAGE we will have one extra band at ~12 kDa for the cleavage product by BoNT/C.

Example for Detection of Toxin in a Food Sample

Food samples are processed to obtain a clear aqueous solution to be tested for toxin detection. SNAMP, or its derivatives, is prepared in a reaction mixture of about 500 ul at a concentration of (1-2 uM). 50-100 ul of test aqueous solution is mixed with the SNAMP solution and incubated for 30-120 min at 37° C. The reaction is stopped with SDS-PAGE sample buffer. The sample is boiled for 1 min before loading on to a polyacrylamide gel for electrophoresis. Electrophoretic protein bands are examined after staining with Coomassie blue for detection of toxin and recognition of serotype.

Advantages of the Invention

Present invention gives a novel SNAMP and SNAMPAXIN universal substrate. The substrate can be cleaved by all the known substrate of BoNT (A-G). The present invention also provides a novel process for the preparation of the universal substrate for in vitro and intracellular assay. The present invention also provides a method for detection of BoNT in clinical and food matrices. The present invention uses cell system containing the new SNAMP or SNAMPAXIN substrate for the assay of different serotypes of BoNT to replace MBA.

CONCLUSION

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Or, the technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed.

The term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3).

As used herein, the term "substantially" refers to approximately the same shape as stated.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments.

Trademarks: the product names used in this document are for identification purposes only; and are the property of their respective owners.

LIST OF REFERENCES CITED

Arnon, S. S., Schechter R., Inglesby T. V., et al. (2001). Botulinum toxin as a biological weapon: medical and public health management. *JAMA,* 285 (20), 1059-70.

Hobbs, R. J., Thomas, C. A., Halliwell, G., et al. (2019). Rapid Detection of Botulinum Neurotoxins—A Review. *Toxins,* 11 (7), 418-430.

Basavanna, U., Muruvanda, T., Brown, E. W., and Sharma, S. K. (2013). Development of a Cell-Based Functional Assay for the Detection of *Clostridium botulinum* Neurotoxin Types A and E. *International Journal of Microbiology*, Article ID 593219, 1-7.

Bitz S (2010) The botulinum neurotoxin LD50 test—problems and solutions. ALTEX 27: 114-116.

Froger, A., and Hall, J. E. (2007). Transformation of plasmid DNA into *E. coli* using the heat shock method. *Journal of visualized experiments: JoVE*, (6), 253.

Li, L., and Singh, B. R. (1999). In vitro translation of type A *Clostridium botulinum* neurotoxin heavy chain and analysis of its binding to rat synaptosomes. *Journal of Protein Chemistry,* 18, 89-95.

Pellett S. (2013). Progress in cell-based assays for botulinum neurotoxin detection. *Current topics in microbiology and immunology,* 364, 257-285.

Schantz, E. J., & Johnson, E. A. (1992). Properties and use of botulinum toxin and other microbial neurotoxins in medicine. *Microbiological reviews,* 56 (1), 80-99.

Straughan D (2006) Progress in applying the Three Rs to the potency testing of Botulinum toxin type A. Altern Lab Anim 34: 305-313.

Taylor K, Gericke C, Alvarez L R (2019) Botulinum toxin testing on animals is still a Europe-wide issue. ALTEX 36: 81-90.

Whitemarsh, R. C., Strathman, M. J., Chase, L. G., et al., (2012) Novel Application of Human Neurons Derived from Induced Pluripotent Stem Cells for Highly Sensitive Botulinum Neurotoxin Detection, *Toxicological Sciences,* 126 (2), 426-435.

Whitemarsh, R. C., Tepp, W. H., Bradshaw, M., et al. (2013). Characterization of botulinum neurotoxin A subtypes 1 through 5 by investigation of activities in mice, in neuronal cell cultures, and in vitro. *Infection and immunity,* 81(10), 3894-3902.

OTHER REFERENCES CITED

US patent application 20140235490 by City of Hope that was published on Aug. 21, 2014.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the scope of the appended claims.

What is claimed is:

1. A method for detecting and assaying the presence of a *Clostridium* neurotoxin in a sample comprising:

a) providing a universal recombinant substrate fusion protein comprising:

i) a human SNAP-25 amino acid sequence of as set forth in SEQ ID NO: 1 from amino acid 141 to 206;

ii) a human VAMP amino acid sequence of as set forth in SEQ ID NO: 4 from amino acid 27 to 93, iii) a human syntaxin amino acid sequence as set forth in SEQ ID NO: 5 from amino acid 221-264;

iv) at least one Förster resonance energy transfer (FRET) or a luminescence reporter;

b) exposing the sample containing a *Clostridium* neurotoxin to a sample comprising the universal recombinant substrate fusion protein capable of producing a detectable Förster resonance energy transfer (FRET), or a luminescence signal change, following cleavage of the universal recombinant substrate fusion protein by the *Clostridium* neurotoxin;

c) detecting and assaying the presence of the *Clostridium* neurotoxin by measuring a change in the Förster resonance energy transfer or the luminescence signal in the sample; and d) determining an electrophoretic mobility pattern of one or more cleaved protein bands or a degraded protein, using a high throughput automated system to identify one or more serotypes of the *Clostridium* neurotoxin and tetanus.

2. The method of claim 1, wherein the *Clostridium* neurotoxin is a tetanus neurotoxin.

3. The method of claim 1, wherein the *Clostridium* neurotoxin is a botulinum neurotoxin serotype A, B, C, D, E, F or G.

4. The method of claim 3, wherein when the botulinum neurotoxin is the serotype A or C, and the universal recombinant substrate fusion protein comprises SEQ ID NO: 3.

5. The method of claim 3, wherein the botulinum neurotoxin is in an active form of botulinum neurotoxin serotype A or C.

6. The method of claim 1, wherein the universal recombinant substrate fusion protein comprises: two opposing FRET or luminescence reporters positioned with the sequences of (i, ii, iii) in between said reporters.

7. The method of claim 6, wherein the SNAMP universal recombinant substrate fusion protein further comprises the human syntaxin amino acid sequence as set forth in SEQ ID NO: 5.

8. The method of claim 7, wherein the Förster resonance energy transfer (FRET) reporter is an Enhanced Green Fluorescence Protein (EGFP), a red fluorescent protein (RFP), a cyan fluorescent protein (CFP), a yellow fluorescent protein (YFP), a blue fluorescent protein (BFP) or combinations thereof.

9. The method of claim 7, wherein the SNAMP universal recombinant substrate fusion protein comprises: i, ii, iii fused together N terminus to C terminus.

10. The method of claim 1, wherein the SNAMP universal recombinant substrate fusion protein comprises the amino acid sequence of SEQ ID NO: 2.

11. The method of claim 9, wherein the universal recombinant substrate fusion protein further comprises the human syntaxin amino acid sequence as set forth in SEQ ID NO: 5, amino acids 221-264.

12. The method of claim 1, wherein the universal recombinant substrate fusion protein comprises: the human SNAP-25 sequence of SEQ ID NO: 1; the human VAMP sequence of SEQ ID NO: 4; and the syntaxin protein of SEQ ID NO: 5 to provide a SNAMPAXIN recombinant substrate fusion protein of SEQ ID NO: 3.

13. The method of claim 7, wherein the universal recombinant substrate fusion protein comprises: the human SNAP-25 of SEQ ID NO: 1; the human VAMP of SEQ ID NO: 4; the syntaxin protein of SEQ ID NO: 5; and, the Förster resonance energy transfer (FRET) or Luminescence reporter to provide a SNAMPAXIN recombinant universal substrate fusion protein.

14. The method of claim 11, wherein the human syntaxin sequence is the amino acid 221 to the amino acid 24 of SEQ ID NO: 5.

15. The method of claim 1, wherein the universal recombinant substrate fusion protein is expressed in *E. Coli* using a vector encoding in order: a red fluorescent protein (RFP); the human SNAP-25 protein; the human VAMP protein; and an Enhanced Green Fluorescence Protein (EGFP).

16. The method of claim 4, wherein the universal recombinant substrate fusion protein is tagged by GST or Histidine.

17. The method of claim 4, wherein the universal recombinant substrate fusion protein comprises an amino acid sequence of SEQ ID NO: 3.

18. The method of claim 1, wherein the sample is a food sample, or a blood or a serum sample from a human or an animal.

19. A method for detecting and assaying the presence of a *Clostridium* neurotoxin in a sample comprising:

a) providing a universal recombinant substrate fusion protein comprising:

i) an amino acid sequence comprising a SNAP25-VAMP-SYNTAXIN fusion protein comprising SEQ ID NO: 3;

ii) one or more Förster resonance energy transfer (FRET) or a luminescence reporters flanking SEQ ID NO: 3;

b) exposing the sample containing a *Clostridium* neurotoxin to a sample comprising the universal recombinant substrate fusion protein capable of producing a detectable Förster resonance energy transfer (FRET), or a luminescence signal change, following cleavage of the universal recombinant substrate fusion protein by the *Clostridium* neurotoxin;

c) detecting and assaying the presence of the *Clostridium* neurotoxin type A, B, C, D, E, F or G and tetanus by measuring a change in the Förster resonance energy transfer or the luminescence signal in the sample; and d) determining an electrophoretic mobility pattern of one or more cleaved protein bands or a degraded protein, using a high throughput automated system to identify one or more serotypes of the *Clostridium* neurotoxin.

* * * * *

SEQUENCE LISTING

```
<160> NUMBER OF SEQ ID NOS: 5

<210> SEQ ID NO 1
<211> LENGTH: 206
```

```
<212> TYPE: PRT
<213> ORGANISM: Homo sapiens
<220> FEATURE:
<221> NAME/KEY: SNAP-25
<222> LOCATION: (1)..(206)

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 2
<211> LENGTH: 831
<212> TYPE: PRT
<213> ORGANISM: Homo sapiens
<220> FEATURE:
<221> NAME/KEY: SNAMP
<222> LOCATION: (1)..(831)
<223> OTHER INFORMATION: SNAMP

<400> SEQUENCE: 2

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110
```

```
Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Gly Met Asp Asn Thr Glu Asp Val Ile Lys Glu Phe Met Gln
225                 230                 235                 240

Phe Lys Val Arg Met Glu Gly Ser Val Asn Gly His Tyr Phe Glu Ile
                245                 250                 255

Glu Gly Glu Gly Glu Gly Lys Pro Tyr Glu Gly Thr Gln Thr Ala Lys
            260                 265                 270

Leu Gln Val Thr Lys Gly Gly Pro Leu Pro Phe Ala Trp Asp Ile Leu
        275                 280                 285

Ser Pro Gln Phe Gln Tyr Gly Ser Lys Ala Tyr Val Lys His Pro Ala
    290                 295                 300

Asp Ile Pro Asp Tyr Met Lys Leu Ser Phe Pro Glu Gly Phe Thr Trp
305                 310                 315                 320

Glu Arg Ser Met Asn Phe Glu Asp Gly Gly Val Val Glu Val Gln Gln
                325                 330                 335

Asp Ser Ser Leu Gln Asp Gly Thr Phe Ile Tyr Lys Val Lys Phe Lys
            340                 345                 350

Gly Val Asn Phe Pro Ala Asp Gly Pro Val Met Gln Lys Lys Thr Ala
        355                 360                 365

Gly Trp Glu Pro Ser Thr Glu Lys Leu Tyr Pro Gln Asp Gly Val Leu
    370                 375                 380

Lys Gly Glu Ile Ser His Ala Leu Lys Leu Lys Asp Gly Gly His Tyr
385                 390                 395                 400

Thr Cys Asp Phe Lys Thr Val Tyr Lys Ala Lys Lys Pro Val Gln Leu
                405                 410                 415

Pro Gly Asn His Tyr Val Asp Ser Lys Leu Asp Ile Thr Asn His Asn
            420                 425                 430

Glu Asp Tyr Thr Val Val Glu Gln Tyr Glu His Ala Glu Ala Arg His
        435                 440                 445

Ser Gly Ser Gln Ser Ala Arg Glu Asn Glu Met Asp Glu Asn Leu Glu
    450                 455                 460

Gln Val Ser Gly Ile Ile Gly Asn Leu Arg His Met Ala Leu Asp Met
465                 470                 475                 480

Gly Asn Glu Ile Asp Thr Gln Asn Arg Gln Ile Asp Arg Ile Met Glu
                485                 490                 495

Lys Ala Asp Ser Asn Lys Thr Arg Ile Asp Glu Ala Asn Gln Arg Ala
            500                 505                 510

Thr Lys Met Leu Gly Ser Gly Thr Ser Asn Arg Arg Leu Gln Gln Thr
        515                 520                 525
```

```
Gln Ala Gln Val Asp Glu Val Val Asp Ile Met Arg Val Asn Val Asp
    530                 535                 540

Lys Val Leu Glu Arg Asp Gln Lys Leu Ser Glu Leu Asp Asp Arg Ala
545                 550                 555                 560

Asp Ala Leu Gln Ala Gly Ala Ser Gln Phe Glu Thr Ser Ala Ala Lys
                565                 570                 575

Leu Lys Arg Lys Tyr Trp Trp Lys Asn Leu Lys Leu Pro Val Ala Thr
            580                 585                 590

Met Val Ser Lys Gly Glu Glu Leu Phe Thr Gly Val Val Pro Ile Leu
        595                 600                 605

Val Glu Leu Asp Gly Asp Val Asn Gly His Lys Phe Ser Val Ser Gly
    610                 615                 620

Glu Gly Glu Gly Asp Ala Thr Tyr Gly Lys Leu Thr Leu Lys Phe Ile
625                 630                 635                 640

Cys Thr Thr Gly Lys Leu Pro Val Pro Trp Pro Thr Leu Val Thr Thr
                645                 650                 655

Leu Thr Tyr Gly Val Gln Cys Phe Ser Arg Tyr Pro Asp His Met Lys
            660                 665                 670

Gln His Asp Phe Phe Lys Ser Ala Met Pro Glu Gly Tyr Val Gln Glu
        675                 680                 685

Arg Thr Ile Phe Phe Lys Asp Asp Gly Asn Tyr Lys Thr Arg Ala Glu
    690                 695                 700

Val Lys Phe Glu Gly Asp Thr Leu Val Asn Arg Ile Glu Leu Lys Gly
705                 710                 715                 720

Ile Asp Phe Lys Glu Asp Gly Asn Ile Leu Gly His Lys Leu Glu Tyr
                725                 730                 735

Asn Tyr Asn Ser His Asn Val Tyr Ile Met Ala Asp Lys Gln Lys Asn
            740                 745                 750

Gly Ile Lys Val Asn Phe Lys Ile Arg His Asn Ile Glu Asp Gly Ser
        755                 760                 765

Val Gln Leu Ala Asp His Tyr Gln Gln Asn Thr Pro Ile Gly Asp Gly
    770                 775                 780

Pro Val Leu Leu Pro Asp Asn His Tyr Leu Ser Thr Gln Ser Ala Leu
785                 790                 795                 800

Ser Lys Asp Pro Asn Glu Lys Arg Asp His Met Val Leu Leu Glu Phe
                805                 810                 815

Val Thr Ala Ala Gly Ile Thr Leu Gly Met Asp Glu Leu Tyr Lys
            820                 825                 830


<210> SEQ ID NO 3
<211> LENGTH: 899
<212> TYPE: PRT
<213> ORGANISM: Homo sapiens
<220> FEATURE:
<221> NAME/KEY: SNAMPAXIN
<222> LOCATION: (1)..(899)
<223> OTHER INFORMATION: SNAMPAXIN

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
```

```
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Gly Met Asp Asn Thr Glu Asp Val Ile Lys Glu Phe Met Gln
225                 230                 235                 240

Phe Lys Val Arg Met Glu Gly Ser Val Asn Gly His Tyr Phe Glu Ile
                245                 250                 255

Glu Gly Glu Gly Glu Gly Lys Pro Tyr Glu Gly Thr Gln Thr Ala Lys
            260                 265                 270

Leu Gln Val Thr Lys Gly Gly Pro Leu Pro Phe Ala Trp Asp Ile Leu
        275                 280                 285

Ser Pro Gln Phe Gln Tyr Gly Ser Lys Ala Tyr Val Lys His Pro Ala
    290                 295                 300

Asp Ile Pro Asp Tyr Met Lys Leu Ser Phe Pro Glu Gly Phe Thr Trp
305                 310                 315                 320

Glu Arg Ser Met Asn Phe Glu Asp Gly Gly Val Val Glu Val Gln Gln
                325                 330                 335

Asp Ser Ser Leu Gln Asp Gly Thr Phe Ile Tyr Lys Val Lys Phe Lys
            340                 345                 350

Gly Val Asn Phe Pro Ala Asp Gly Pro Val Met Gln Lys Lys Thr Ala
        355                 360                 365

Gly Trp Glu Pro Ser Thr Glu Lys Leu Tyr Pro Gln Asp Gly Val Leu
    370                 375                 380

Lys Gly Glu Ile Ser His Ala Leu Lys Leu Lys Asp Gly Gly His Tyr
385                 390                 395                 400

Thr Cys Asp Phe Lys Thr Val Tyr Lys Ala Lys Lys Pro Val Gln Leu
                405                 410                 415

Pro Gly Asn His Tyr Val Asp Ser Lys Leu Asp Ile Thr Asn His Asn
            420                 425                 430

Glu Asp Tyr Thr Val Val Glu Gln Tyr Glu His Ala Glu Ala Arg His
        435                 440                 445

Ser Gly Ser Gln Ser Ala Arg Glu Asn Glu Met Asp Glu Asn Leu Glu
    450                 455                 460

Gln Val Ser Gly Ile Ile Gly Asn Leu Arg His Met Ala Leu Asp Met
465                 470                 475                 480
```

-continued

```
Gly Asn Glu Ile Asp Thr Gln Asn Arg Gln Ile Asp Arg Ile Met Glu
                485                 490                 495

Lys Ala Asp Ser Asn Lys Thr Arg Ile Asp Glu Ala Asn Gln Arg Ala
            500                 505                 510

Thr Lys Met Leu Gly Ser Gly Thr Ser Asn Arg Arg Leu Gln Gln Thr
        515                 520                 525

Gln Ala Gln Val Asp Glu Val Val Asp Ile Met Arg Val Asn Val Asp
    530                 535                 540

Lys Val Leu Glu Arg Asp Gln Lys Leu Ser Glu Leu Asp Asp Arg Ala
545                 550                 555                 560

Asp Ala Leu Gln Ala Gly Ala Ser Gln Phe Glu Thr Ser Ala Ala Lys
                565                 570                 575

Leu Lys Arg Lys Tyr Trp Trp Lys Asn Leu Lys Met Leu Val Glu Ser
            580                 585                 590

Gln Gly Glu Met Ile Asp Arg Ile Glu Tyr Asn Val Glu His Ala Val
        595                 600                 605

Asp Tyr Val Glu Arg Ala Val Ser Asp Thr Lys Lys Ala Val Lys Tyr
    610                 615                 620

Gln Ser Lys Ala Arg Arg Lys Lys Ile Met Ile Ile Ile Cys Cys Val
625                 630                 635                 640

Ile Leu Gly Ile Val Ile Ala Ser Thr Val Gly Gly Ile Phe Ala Leu
                645                 650                 655

Pro Val Ala Thr Met Val Ser Lys Gly Glu Glu Leu Phe Thr Gly Val
            660                 665                 670

Val Pro Ile Leu Val Glu Leu Asp Gly Asp Val Asn Gly His Lys Phe
        675                 680                 685

Ser Val Ser Gly Glu Gly Glu Gly Asp Ala Thr Tyr Gly Lys Leu Thr
    690                 695                 700

Leu Lys Phe Ile Cys Thr Thr Gly Lys Leu Pro Val Pro Trp Pro Thr
705                 710                 715                 720

Leu Val Thr Thr Leu Thr Tyr Gly Val Gln Cys Phe Ser Arg Tyr Pro
                725                 730                 735

Asp His Met Lys Gln His Asp Phe Phe Lys Ser Ala Met Pro Glu Gly
            740                 745                 750

Tyr Val Gln Glu Arg Thr Ile Phe Phe Lys Asp Asp Gly Asn Tyr Lys
        755                 760                 765

Thr Arg Ala Glu Val Lys Phe Glu Gly Asp Thr Leu Val Asn Arg Ile
    770                 775                 780

Glu Leu Lys Gly Ile Asp Phe Lys Glu Asp Gly Asn Ile Leu Gly His
785                 790                 795                 800

Lys Leu Glu Tyr Asn Tyr Asn Ser His Asn Val Tyr Ile Met Ala Asp
                805                 810                 815

Lys Gln Lys Asn Gly Ile Lys Val Asn Phe Lys Ile Arg His Asn Ile
            820                 825                 830

Glu Asp Gly Ser Val Gln Leu Ala Asp His Tyr Gln Gln Asn Thr Pro
        835                 840                 845

Ile Gly Asp Gly Pro Val Leu Leu Pro Asp Asn His Tyr Leu Ser Thr
    850                 855                 860

Gln Ser Ala Leu Ser Lys Asp Pro Asn Glu Lys Arg Asp His Met Val
865                 870                 875                 880

Leu Leu Glu Phe Val Thr Ala Ala Gly Ile Thr Leu Gly Met Asp Glu
                885                 890                 895
```

Leu Tyr Lys

<210> SEQ ID NO 4
<211> LENGTH: 93
<212> TYPE: PRT
<213> ORGANISM: Homo sapiens
<220> FEATURE:
<221> NAME/KEY: VAMP-2
<222> LOCATION: (1)..(93)
<223> OTHER INFORMATION: VAMP-2

<400> SEQUENCE: 4

```
Ser Ala Thr Ala Ala Thr Ala Pro Pro Ala Ala Pro Ala Gly Glu Gly
1               5                   10                  15

Gly Pro Pro Ala Pro Pro Pro Asn Leu Thr Ser Asn Arg Arg Leu Gln
            20                  25                  30

Gln Thr Gln Ala Gln Val Asp Glu Val Val Asp Ile Met Arg Val Asn
        35                  40                  45

Val Asp Lys Val Leu Glu Arg Asp Gln Lys Leu Ser Glu Leu Asp Asp
    50                  55                  60

Arg Ala Asp Ala Leu Gln Ala Gly Ala Ser Gln Phe Glu Thr Ser Ala
65                  70                  75                  80

Ala Lys Leu Lys Arg Lys Tyr Trp Trp Lys Asn Leu Lys
                85                  90
```

<210> SEQ ID NO 5
<211> LENGTH: 264
<212> TYPE: PRT
<213> ORGANISM: Homo sapiens
<220> FEATURE:
<221> NAME/KEY: SYNTAXIN
<222> LOCATION: (1)..(264)
<223> OTHER INFORMATION: SYNTAXIN

<400> SEQUENCE: 5

```
Met Lys Asp Arg Thr Gln Glu Leu Arg Ser Ala Lys Asp Ser Asp Asp
1               5                   10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190
```

-continued

```
Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys
            260
```